(12) United States Patent
Han et al.

(10) Patent No.: US 10,627,349 B2
(45) Date of Patent: Apr. 21, 2020

(54) SIGNAL PROCESSING DEVICE OF ANALYZING BIO-SIGNAL AND BIO-SIGNAL ANALYZING APPARATUS USING THE SAME

(71) Applicant: OLIVE HEALTHCARE INC., Seoul (KR)

(72) Inventors: Sung Ho Han, Seoul (KR); Keun Sik No, Yongin-si (KR); Hee Sun Hong, Seoul (KR)

(73) Assignee: OLIVE HEALTHCARE INC., Seoul (KR)

(*) Notice: Subject to any disclaimer, the term of this patent is extended or adjusted under 35 U.S.C. 154(b) by 0 days.

(21) Appl. No.: 16/189,393

(22) Filed: Nov. 13, 2018

(65) Prior Publication Data

US 2019/0257759 A1 Aug. 22, 2019

Related U.S. Application Data

(63) Continuation-in-part of application No. PCT/KR2018/002619, filed on Mar. 6, 2018.

(30) Foreign Application Priority Data

Feb. 21, 2018 (KR) .................. 10-2018-0020555

(51) Int. Cl.
*A61B 5/1455* (2006.01)
*G01N 21/64* (2006.01)
(Continued)

(52) U.S. Cl.
CPC ....... *G01N 21/6486* (2013.01); *A61B 5/1455* (2013.01); *G01N 21/31* (2013.01);
(Continued)

(58) Field of Classification Search
CPC . A61B 5/00; A61B 6/00; G01N 21/00; G01N 2021/1736
See application file for complete search history.

(56) References Cited

U.S. PATENT DOCUMENTS

2002/0032531 A1* 3/2002 Mansky ............... B01J 19/0046
702/21
2004/0039267 A1 2/2004 Kawasaki et al.
(Continued)

FOREIGN PATENT DOCUMENTS

EP 1380253 1/2004
JP 09098972 4/1997
(Continued)

OTHER PUBLICATIONS

International Search Report—PCT/KR2018/002619 dated Oct. 12, 2018.
(Continued)

*Primary Examiner* — David P Porta
*Assistant Examiner* — Mamadou Faye
(74) *Attorney, Agent, or Firm* — Cantor Colburn LLP

(57) ABSTRACT

A signal processing device that processes a bio-signal includes a lock-in amplifier chip configured to output a frequency-modulated modulation signal and enable one or more light sources to be driven in response to the modulation signal, and a multiplexer configured to receive and multiplex light sensing signals output from the light sources and then measured by multiple light measurement units, and the lock-in amplifier chip sequentially demodulates the multiple light sensing signals transmitted through the multiplexer.

19 Claims, 4 Drawing Sheets

(51) Int. Cl.
*G01N 21/31* (2006.01)
*G01N 21/35* (2014.01)
*G01N 21/49* (2006.01)

(52) U.S. Cl.
CPC ......... *G01N 21/314* (2013.01); *G01N 21/35* (2013.01); *G01N 21/49* (2013.01); *G01N 2021/3129* (2013.01); *G01N 2201/12* (2013.01)

(56) References Cited

U.S. PATENT DOCUMENTS

| | | | |
|---|---|---|---|
| 2004/0072278 A1* | 4/2004 | Chou | B01L 3/502761 435/29 |
| 2005/0243322 A1* | 11/2005 | Lasker | G01N 21/4795 356/432 |
| 2006/0184045 A1 | 8/2006 | Yamashita et al. | |
| 2008/0177163 A1* | 7/2008 | Wang | A61B 5/0073 600/324 |
| 2011/0118571 A1 | 5/2011 | Mandelis et al. | |
| 2014/0039341 A1* | 2/2014 | Bohorquez | A61B 5/0537 600/547 |
| 2015/0173621 A1 | 6/2015 | Guo et al. | |

FOREIGN PATENT DOCUMENTS

| | | |
|---|---|---|
| JP | 2000023947 | 1/2000 |
| JP | 2003526091 | 9/2003 |
| JP | 6220065 | 10/2017 |

OTHER PUBLICATIONS

European Search Report—European Application No. 188008221, dated Nov. 26, 2019, citing US 2015/173621, EP 1 380 253, US 2006/184045, US 2004/039267 and Ananlog Devices.
Synchronous Demodulator and Configurable Analog Filter, Analog Devices, 2014, pp. 1-24.

\* cited by examiner

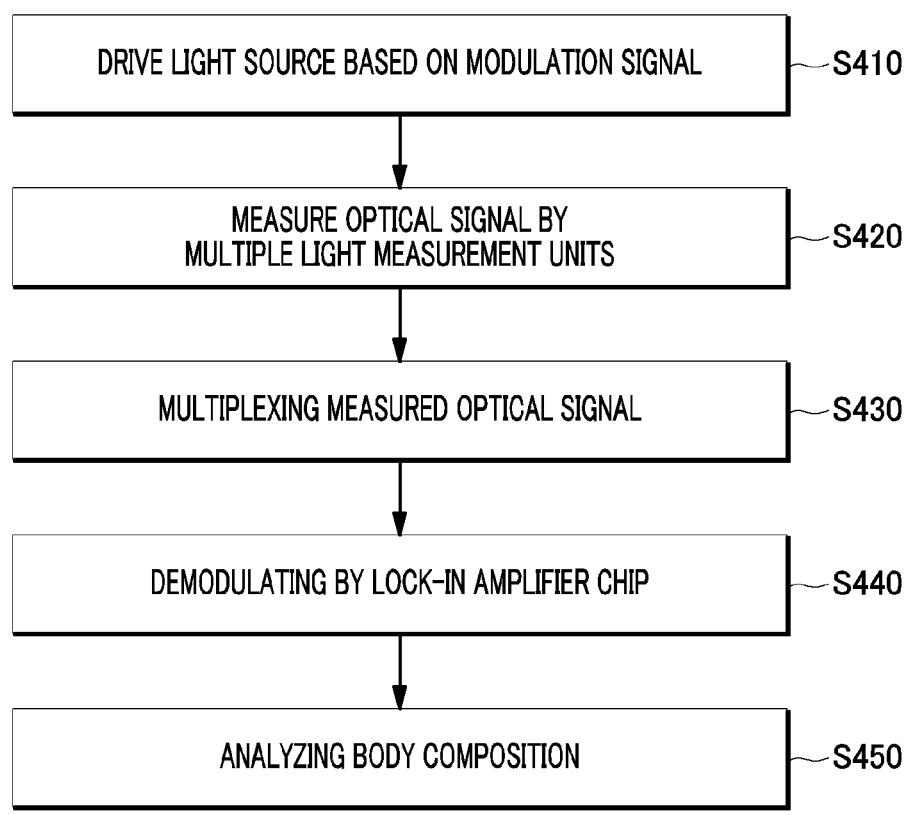

SIGNAL PROCESSING DEVICE OF ANALYZING BIO-SIGNAL AND BIO-SIGNAL ANALYZING APPARATUS USING THE SAME

TECHNICAL FIELD

The present disclosure relates to a signal processing device of analyzing a bio-signal and a bio-signal analyzing apparatus using the same.

BACKGROUND

Recently, various techniques for analyzing biometric data of the body using a method for measuring the optical properties of a turbid medium are being developed. These techniques have attracted a lot of attention in that they are non-invasive and can provide biometric data, and a lot of attention is being focused on research for development into entry-level devices according to the needs of consumers.

These techniques generally calculate the concentration of a chromophore in the turbid medium by measuring the absorption coefficient and the scattering coefficient of a turbid medium in a near infrared ray region. There are three methods known to measure the absorption coefficient and the scattering coefficient of a turbid medium. Specifically, these methods include a steady-state (SS) method of irradiating light of a predetermined intensity into a turbid medium and calculating the concentration of a chromophore according to a multi-distance measurement method, a frequency domain (FD) method of measuring a changed amplitude and phase for a modulated light source, and a time domain (TD) method of measuring a change over time for a pulse-type light source.

The SS method does not require the modulation of light or pulse generation and thus does not require a detector that decomposes light reflected from a turbid medium by frequency domain or time domain. Therefore, the SS method is cheaper than the other methods (i.e., FD method or TD method). However, the SS method uses the multi-distance measurement method to separate the absorption coefficient and the scattering coefficient. Therefore, in biological tissue with high non-uniformity, the SS method is more likely to generate distortion during analysis than the other methods.

The TD method and the FD method do not use multi-distance measurement method and thus are more suitable for biological tissue with non-uniformity than the SS method. However, the TD method and the FD method require a detector configured to detect pulse generation or frequency-modulated light source and the properties thereof. Therefore, the TD method and the FD method have shortcomings in terms of implementation and cost.

The present disclosure adopts the steady state (SS) method but uses a lock-in amplifier structure to minimize the effect of ambient light and implement a high signal-to-noise ratio (SNR). The lock-in amplifier refers to an amplifier configured to recover a signal in noise and has been used to remove a noise which is much greater than a signal to be detected. The lock-in amplifier may multiply a target signal with a specific frequency and a reference signal with the same frequency as the target signal, to extract a magnitude of the target signal. For example, if a noise is included in a broad frequency band including a frequency (fa) of the signal to be detected, the signal to be detected and the reference signal having the same frequency as the signal to be detected are multiplied to obtain a harmonic wave (2fa) which is the sum of the two frequencies and a direct current (DC) which is the difference between the frequencies. An intensity of the direct current (DC) which is the difference between the frequencies is proportional to an amplitude of the signal to be detected. If a low-pass filter is applied to the signal obtained in this way, the sum of the frequencies is removed and only the difference between the frequencies is obtained. As such, if a signal only in a direct current (DC) band is detected using the lock-in amplifier, a level of the signal to be detected is not changed but a magnitude of the noise is decreased, and, thus, it is possible to effectively remove a noise generated outside the detection device.

However, in order to effectively remove a noise by a bio-signal analyzing apparatus including the above-described multiple light sources and multiple light detectors, a new method is needed.

DISCLOSURE OF THE INVENTION

Problems to be Solved by the Invention

The present disclosure is conceived to solve the above-described problem of the conventional technology and provides a signal processing device capable of effectively removing a noise from multiple optical signals measured by multiple light measurement units and a bio-signal analyzing apparatus using the same.

However, problems to be solved by the present disclosure are not limited to the above-described problems. There may be other problems to be solved by the present disclosure.

Means for Solving the Problems

As a technical means for solving the above-described technical problems, a signal processing device that processes a bio-signal according to a first aspect of the present disclosure includes: a lock-in amplifier chip configured to output a frequency-modulated modulation signal and enable one or more light sources to be driven in response to the modulation signal; and a multiplexer configured to receive and multiplex light sensing signals output from the light sources and then measured by multiple light measurement units. Herein, the lock-in amplifier chip sequentially demodulates the multiple light sensing signals transmitted through the multiplexer.

Further, a body composition analyzing apparatus that analyzes a bio-signal according to a second aspect of the present disclosure includes: multiple light sources; multiple light measurement units; a signal processing unit configured to transmit a frequency-modulated modulation signal to the light sources through a lock-in amplifier chip, receive light sensing signals measured by the light measurement units, and remove a noise from the light sensing signals through the lock-in amplifier chip; and a body composition analyzing unit configured to analyze body composition of a subject based on a signal output from the signal processing unit.

Furthermore, a method of analyzing body composition by analyzing a bio-signal according to a third aspect of the present disclosure includes: outputting optical signals by multiple light sources based on a modulation signal whose frequency is modulated by a lock-in amplifier chip; measuring the optical signals, which are output from the multiple light sources and reflected from a subject, by multiple light measurement units, respectively; multiplexing multiple light sensing signals measured by the respective multiple light measurement units and then sequentially outputting the multiple light sensing signals by a multiplexer; receiving, demodulating, and outputting the sequentially output multiple light sensing signals by the lock-in amplifier chip; and analyzing body composition of a subject based on the signals output from the lock-in amplifier chip.

Effects of the Invention

According to the above-described technical means for solving technical problems of the present disclosure, when a noise in optical signals sensed by multiple light measurement units is removed, the noise in the multiple optical signals can be removed using only a single lock-in amplifier chip. Thus, the presented invention can not only reduce the size of a bio-signal analyzing apparatus but also reduce the cost to be used for components of the bio-signal analyzing apparatus.

BRIEF DESCRIPTION OF THE DRAWINGS

FIG. 4 is a flowchart provided to explain a method of analyzing body composition according to an embodiment of the present disclosure.

MODE FOR CARRYING OUT THE INVENTION

Figure 1:
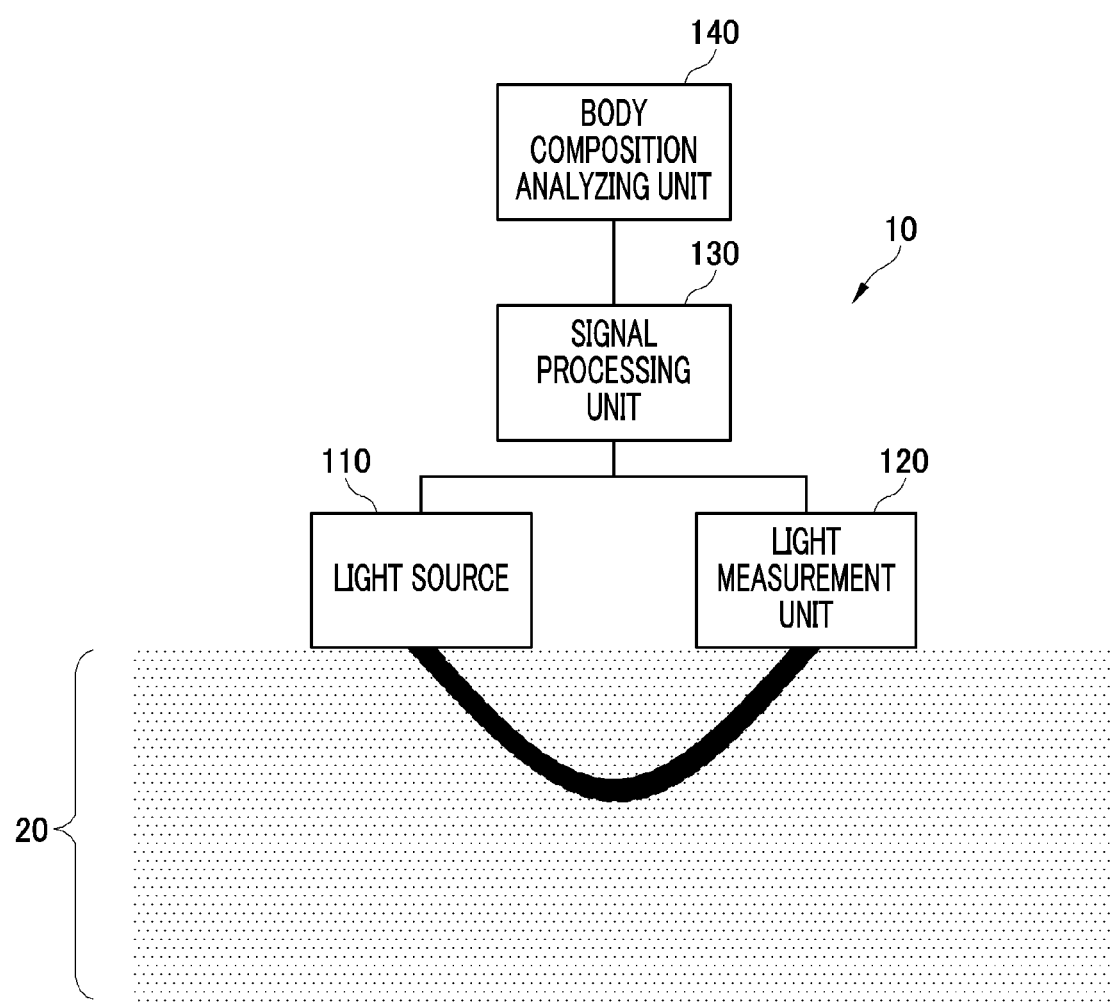
FIG. 1 is a diagram illustrating a configuration of a lock-in amplifier-based multi-wavelength bio-signal analyzing apparatus according to an embodiment of the present disclosure.

Hereinafter, embodiments of the present disclosure will be described in detail with reference to the accompanying drawings so that the present disclosure may be readily implemented by a person with ordinary skill in the art. However, it is to be noted that the present disclosure is not limited to the embodiments but can be embodied in various other ways. In drawings, parts irrelevant to the description are omitted for the simplicity of explanation, and like reference numerals denote like parts through the whole document.

Through the whole document, the term "connected to" or "coupled to" that is used to designate a connection or coupling of one element to another element includes both a case that an element is "directly connected or coupled to" another element and a case that an element is "electronically connected or coupled to" another element via still another element. Further, the term "comprises or includes" and/or "comprising or including" used in the document means that one or more other components, steps, operation and/or existence or addition of elements are not excluded in addition to the described components, steps, operation and/or elements unless context dictates otherwise.

Furthermore, through the whole document, the term "object" refers to a target to be measured by a multi-wavelength bio-signal analyzing apparatus of the present disclosure and may include a person or animal or a part thereof. Also, the object may include various organs such as the skin surface, the heart, brain, or blood vessels or a variety of phantoms.

FIG. 1 is a diagram illustrating a configuration of a lock-in amplifier-based multi-wavelength bio-signal analyzing apparatus (hereinafter, referred to as "bio-signal analyzing apparatus") according to an embodiment of the present disclosure.

As shown in FIG. 1, a bio-signal analyzing apparatus 10 according to an embodiment of the present disclosure includes multiple light sources 110, multiple light measurement units 120, a signal processing unit 130, and a body composition analyzing unit 140.

The multiple light sources 110 are driven based on a modulation signal whose frequency is modulated by a lock-in amplifier and irradiates light containing multiple discrete wavelength components. The light sources may be implemented as laser diodes (LDs) or light emitting diodes (LEDs) capable of irradiating frequency-modulated light. Meanwhile, an output light output from each light source 110 may contain multiple discrete wavelength components, and the discrete wavelengths may refer to discontinuous wavelengths in a near infrared ray region. For example, the four or more light sources 110 may be used and each LD may emit light at a wavelength ranging from 650 nm to 1,100 nm (nano-meter).

Further, the discrete wavelengths are determined based on a chromophore present in a subject 20. To be specific, the discrete wavelengths may be determined based on an already-known absorbance of each chromophore. The chromophore refers to an atom or group of atoms that absorbs light. In general, four kinds of chromophores, i.e., oxy-hemoglobin (O2Hb), deoxy-hemoglobin (HHb), water (H2O), and lipid, have been known as chromophores present in the body and affecting an absorption spectrum in the near infrared ray region. These four kinds of chromophores are present at various ratios depending on the tissue site. For example, water (H2O), lipid, oxy-hemoglobin (O2Hb), and deoxy-hemoglobin (HHb) are dominantly present in the tissues of arms, legs, etc., and H2O, oxy-hemoglobin, and deoxy-hemoglobin except lipid are dominantly present in the brain.

In general, chromophores have their own absorption spectrum in a near infrared ray region. Water shows a peak around the 980 nm wavelength region and lipid shows a peak around the 930 nm wavelength region. Further, oxy-hemoglobin and deoxy-hemoglobin intersect each other at an isosbestic point around the 800 nm wavelength region. According to an embodiment, the bio-signal analyzing apparatus 10 includes four light sources 110 and may irradiate frequency-modulated light at four discrete wavelengths determined based on the absorbance of water, lipid, oxy-hemoglobin, and deoxy-hemoglobin. To be specific, the four discrete wavelengths include a first discrete wavelength adjacent to the peak region of water and a second discrete wavelength adjacent to the peak region of lipid, and may include a third discrete wavelength before the isosbestic point of the already-known absorption spectrum of oxy-hemoglobin and deoxy-hemoglobin and a fourth discrete wavelength in a region adjacent to the isosbestic point. Herein, the third discrete wavelength may be selected from a region in which oxy-hemoglobin and deoxy-hemoglobin have a relatively big difference in absorption in consideration of the absorbance of deoxy-hemoglobin. For example, the first discrete wavelength may be about 975 nm and the second discrete wavelength may be about 915 nm. Further, the third discrete wavelength and the fourth discrete wavelength may be about 688 nm and about 808 nm, respectively, but may not be limited thereto.

According to another embodiment, the bio-signal analyzing apparatus 10 may further include five, six, seven or eight light sources configured to irradiate light at different wavelengths from the first to fourth discrete wavelengths. Therefore, fifth to eight discrete wavelengths to be added may be determined based on unique properties (e.g., peak) shown in absorption spectra of chromophores other than the above-described chromophores (i.e., water, lipid, oxy/deoxy-hemoglobin). For example, the fifth to eight discrete wavelengths to be added may be determined based on peaks in absorption spectra of collagen, melanin, methemoglobin (MetHb), or CO hemoglobin (COHb) other than the above-described chromophores. However, the present disclosure may not be limited thereto, and wavelengths to be added can be selected in consideration of various conditions. For example, wavelengths to be added may be selected based on the centers of gravity of absorption spectra of chromophores.

As such, the bio-signal analyzing apparatus 10 includes four or more light sources 110 determined based on unique properties shown in absorption spectra of chromophores present in the body, and, thus, the body composition analyzing unit 140 can calculate a concentration of each chromophore with more accuracy.

The light measurement unit 120 is configured to detect an output light reflected and introduced from the subject 20. The light measurement unit 120 may convert the detected output light into an electrical signal and provide the electrical signal to the signal processing unit 130.

The light measurement unit 120 may be implemented as an avalanche photodiode (APD), but may not be limited thereto. The light measurement unit 120 may be implemented into various forms, such as a photodiode, a photo transistor, a photo multiplier tube (PMT), a photo cell, and the like. Further, the light measurement unit 120 may be implemented including a new type of photo sensor developed with advances of technology.

Further, the light measurement units 120 may be arranged at a predetermined distance from the light sources 110 to measure light emitted and introduced from the subject.

The signal processing unit 130 receives light sensing signals from the multiple light measurement units 120 and measures the signals using the lock-in amplifier and then transmits the signals to the body composition analyzing unit 140. The detailed configuration of the signal processing unit 130 will be described with reference to the drawing.

Meanwhile, there may be multiple light sources 110 and multiple light measurement units 120, and each light source 110 and each light measurement unit 120 may form a pair facing each other. For example, the arrangement of a first light source and a second light source may be previously determined to sense an output light from a first light measurement unit and an output light from a second light measurement unit, respectively. Then, light sensing signals sensed by the respective light measurement units may be sequentially transmitted to a lock-in amplifier chip 131 to identify which light source each light sensing signal is output from.

Figure 2:
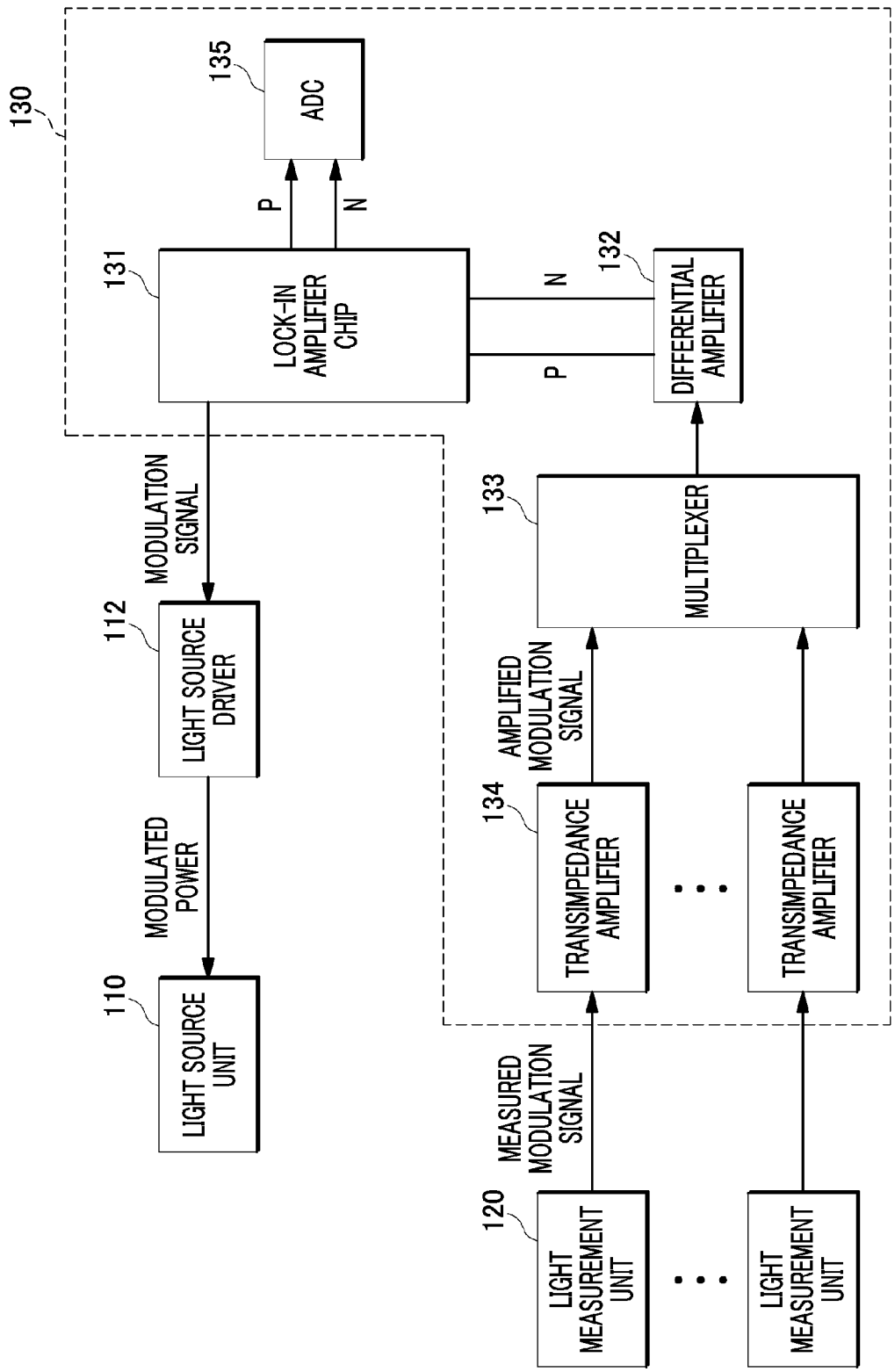
FIG. 2 is a diagram illustrating a detailed configuration of a signal processing unit according to an embodiment of the present disclosure.

FIG. 2 is a diagram illustrating a detailed configuration of a signal processing unit according to an embodiment of the present disclosure.

The signal processing unit 130 includes the lock-in amplifier chip 131, a differential amplifier 132, a multiplexer 133, a transimpedance amplifier 134, and an analog-digital converter 135.

The lock-in amplifier chip 131 is configured to output a frequency-modulated modulation signal. Further, the lock-in amplifier chip 131 multiplies the modulation signal with a reference signal having the same frequency as the modulation signal through a mixer according to a synchronous demodulation method and maintains only a direct current (DC) frequency using a low-pass filter and thus can effectively maintain a desired signal and remove a noise signal.

A single processor equipped with components such as a signal generator, a filter, a mixer (or a phase detector), etc. configured to perform the function of the lock-in amplifier has recently been developed and commercialized (Analog Devices ADA2200), and the lock-in amplifier chip 131 of the present disclosure refers to a part of this integrated processor. Further, refer to the data sheet of the released product for the detailed internal configuration and operation of the lock-in amplifier chip 131, and detailed explanation thereof will be omitted.

A light source driver 112 is configured to receive a frequency-modulated modulation signal supplied from the lock-in amplifier chip 131 and drive the light source 110 based on the modulation signal. Since the light source 110 is driven based on the modulation signal, an optical signal output from the light source 110 also contains a modulated frequency component.

There may be multiple light measurement units 120, and optical signals measured by the respective light measurement units 120 are converted from currents into voltage signals by the transimpedance amplifier 134 and then transmitted to the multiplexer 133. To this end, the transimpedance amplifiers 134 are connected to the multiple light measurement units 120, respectively and signals output from the multiple transimpedance amplifiers 134 are multiplexed by the multiplexer 133 and then transmitted to the lock-in amplifier chip 131. Herein, since the transimpedance amplifiers 134 are connected to the light measurement units 120, respectively, it is possible to set an optimum gain for output power of each optical signal.

The multiplexer 133 is configured to receive light sensing signals measured by the multiple light measurement units 120 through the respective transimpedance amplifiers 134 and multiplex the light sensing signals. Particularly, the multiplexer 133 sequentially transmits the multiple light sensing signals to the lock-in amplifier chip 131 and thus makes it possible to measure signals obtained by removing noise signals as many as possible from light sensing signals measured by multiple light measurement units 120 with only the single lock-in amplifier chip 131.

Further, the multiplexer 133 is configured to sequentially classify the signals received from the respective transimpedance amplifiers 134 and then transmit the signals to the lock-in amplifier chip 131. In this process, some of the light sensing signals may be lost. That is, while the multiplexer 133 transmits a light sensing signal measured by a specific light measurement unit to the lock-in amplifier chip 131, a light sensing signal measured by another light measurement unit may not be transmitted to the lock-in amplifier chip 131 but may be discarded.

Meanwhile, the multiplexer 133 operates as a multiplexer to output any one of light sensing signals in response to a select signal, synchronize the light sensing signal selected by the multiplexer 133 with synchronous demodulation timing of the lock-in amplifier chip 131, and input the light sensing signal output from the multiplexer 133 into the lock-in amplifier chip 131 to remove a noise.

The differential amplifier 132 is configured to receive the output of the multiplexer 133 and differentially amplify the output and then transmit it to the lock-in amplifier chip 131. Therefore, the effect of removing a noise from a light sensing signal can be further improved. A single output unit configured excluding the differential amplifier 132 can be selected by a designer.

The analog-digital converter 135 is configured to convert an output signal generated by the lock-in amplifier chip 131 into a digital one. Further, the analog-digital converter 135 is configured to transmit the converted signal to the body composition analyzing unit 140.

A method of identifying optical signals measured by the respective light measurement units 120 will be described.

The lock-in amplifier chip 131 is configured to supply modulation signals at the same frequency or different frequencies to the respective light sources 110 and perform synchronous demodulation of multiplying each modulation signal and a reference signal with the same or different frequency to remove a noise from the light sensing signals output from the respective measurement units 120. For example, the lock-in amplifier chip 131 performs synchronous demodulation to a modulation signal transmitted from a first light measurement unit based on a first reference signal and synchronous demodulation to a modulation signal transmitted from a second light measurement unit based on a second reference signal.

To this end, in the state where the multiplexer 133 previously sets the sequence and time to output each light sensing signal, the lock-in amplifier chip 131 may perform synchronous demodulation while maintaining or varying a reference frequency according to the sequence to output each light sensing signal.

For example, if modulation signals modulated based on first to fourth frequencies are supplied to first to fourth light sources, light sensing signals sensed by first to fourth light measurement units, respectively, are transmitted to the multiplexer 133. In this case, the multiplexer 133 outputs light sensing signals in sequence from the first light measurement unit to the second light measurement unit to the third light measurement unit then to the fourth light measurement unit and sequentially perform synchronous demodulation to the respective light sensing signals according to the above-described sequence by using the same frequency as the lock-in amplifier chip 131 or different frequencies, i.e., a first frequency, a second frequency, a third frequency, and a fourth frequency.

Further, the body composition analyzing unit 140 is configured to identify output signals of the respective light measurement units in synchronization with light sensing signals of the respective light measurement units output through the ADC 135 after synchronous demodulation in the lock-in amplifier chip and then perform body composition analysis based on the output signals.

The body composition analyzing unit 140 is configured to control overall operations of the bio-signal analyzing apparatus 10. Further, the body composition analyzing unit 140 is configured to perform various kinds of body composition analyses based on the output signals of the respective light measurement units 120 received through the signal processing unit 130.

To this end, the body composition analyzing unit 140 executes a bio-signal analysis program stored in a memory (not illustrated) to control driving of the multiple light sources, calculate a reflectance at each discrete wavelength based on output lights detected from the multiple light measurement units 120, and calculate a concentration of a chromophore present in the subject 20 to analyze body composition of the subject 20. In this case, the body composition analyzing unit 140 may be implemented as a processor used in a general purpose computing device or as an embedded processor.

Firstly, the body composition analyzing unit 140 may determine the number of light sources 110 and light measurement units 120 to be driven based on at least one of the number, content, and kind of at least one chromophore present in the subject 20.

For example, if the number of chromophores present in the subject 20 is four, the body composition analyzing unit 140 may drive at least four light sources 110 based on unique properties of the chromophores shown in the respective absorption spectra.

Then, the body composition analyzing unit 140 may drive the light measurement units 120 to receive output lights detected by the light measurement units 120. Then, the body composition analyzing unit 140 may calculate a reflectance at each discrete wavelength based on the output lights. Details thereof will be described with reference to the drawing.

Figure 3:
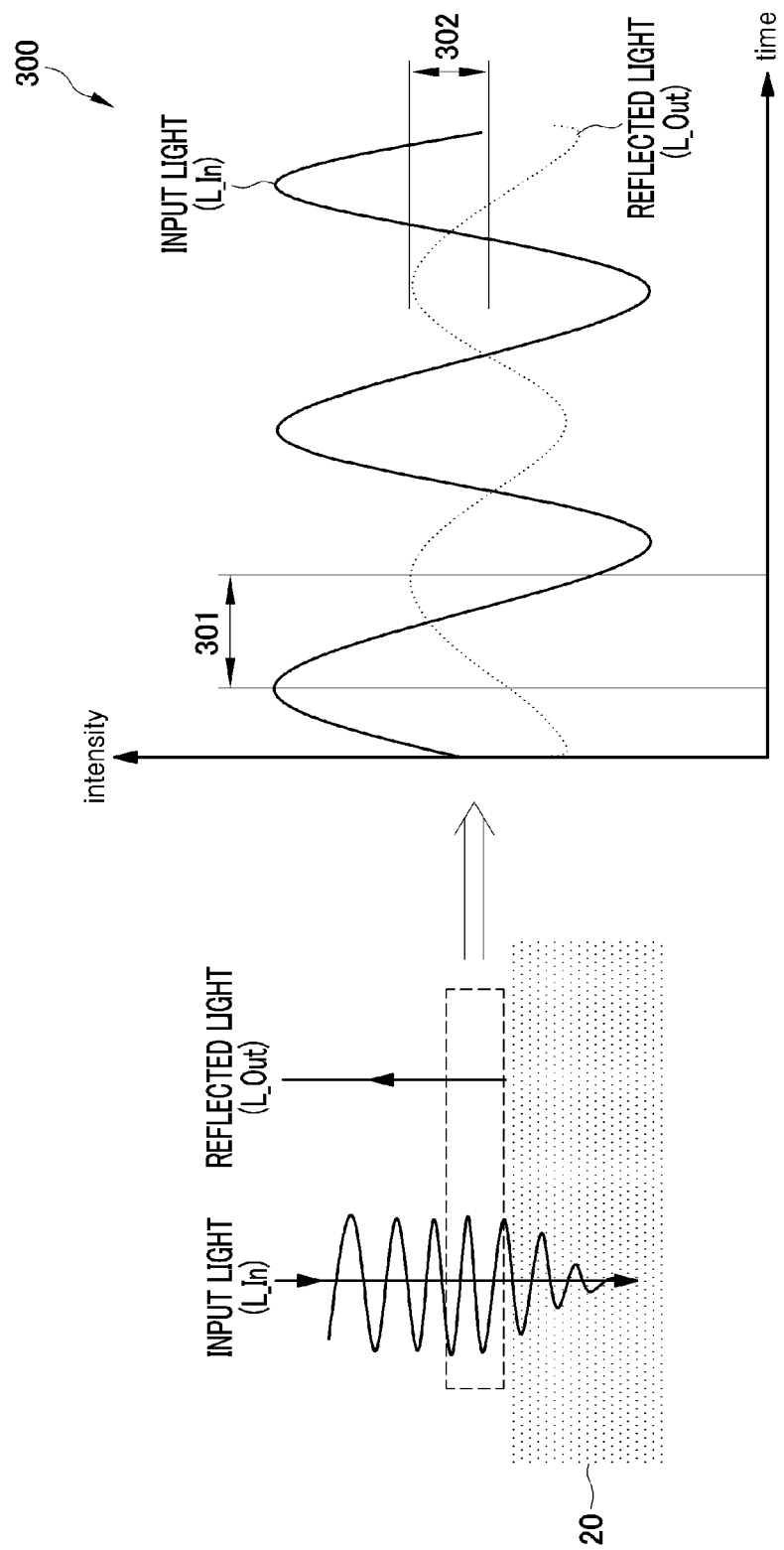
FIG. 3 shows optical characteristics of an input light incident into a subject from a light source and an output light detected by a light measurement unit.

FIG. 3 shows optical characteristics of an input light incident into a subject from a light source and an output light detected by a light measurement unit.

As shown in a right diagram in FIG. 3, if a frequency-modulated input light is irradiated from a light source into the subject 20, the input light is scattered and absorbed by various components including the chromophore present in the subject 20.

A graph 300 shown on the left of FIG. 3 shows properties of an input light L_In and an output light (i.e., reflected light) L_Out in a steady state using a lock-in amplifier. As the frequency-modulated input light L_In is irradiated from the light source into the subject 20, the reflected light L_Out detected by the light measurement unit 120 shows an amplitude attenuation 302 with respect to the input light L_In.

The body composition analyzing unit 140 calculates a reflectance at each discrete wavelength using the amplitude attenuation 302 occurring at each discrete wavelength, and calculates a concentration value of each chromophore based on the calculated reflectance. To this end, the signal processing unit 130 may use diffuse approximation of the radiative transfer equation.

STEP 1: The body composition analyzing unit 140 obtains a diffusion model of a frequency domain calculated using the Green's function in the diffusion approximation. Herein, the diffusion model uses an extrapolated boundary condition as a sample (subject)-air boundary condition. Therefore, the energy fluence at a certain distance $Z_b$ from a surface of the sample is assumed to be 0. $Z_b$ can be defined as shown in the following Equation 1.

$$Z_b = 2D(1+R_{eff})/(1-R_{eff}) \quad \text{[Equation 1]}$$

In the above Equation 1, $R_{eff}$ represents an effective reflectance which is affected by a refractive index. If the sample has a refractive index of 1.4 and the air has a refractive index of 1.0, $R_{eff}$ may be 0.493. Further, D represents a diffusion coefficient and is defined as $l_{tr}/3$. Herein, $l_{tr}$ can be defined as shown in the following Equation 2.

$$l_{tr}(\text{transport mean free path}) = (\mu_a + \mu_s')^{-1} \quad \text{[Equation 2]}$$

Meanwhile, the diffusion model may be previously stored in the memory (not illustrated) of the bio-signal analyzing apparatus 10.

STEP 2: Then, the body composition analyzing unit 140 measures an optical signal based on the lock-in amplifier. The signal processing unit 130 measures an output light corresponding to Equation 3 based on the steady-state method.

$$R(\text{Reflectance Signal}) = C_0 \cdot A \cdot \exp(-i(\varphi + \varphi_0)) \quad \text{[Equation 3]}$$

In the above Equation 3, R represents the measured output light and A and φ represent amplitude and phase components of a signal reflected and introduced from the subject in the measured output light. Further, $C_O$ and $\varphi_O$ represent the amplitude and phase included in the output light due to device itself regardless of a subject. $C_O$ required for calculation is calculated by calibration in the following STEP 2-1.

STEP 2-1: The body composition analyzing unit 140 can calculate a value of $C_O$ before measuring a subject. To be specific, the signal processing unit 130 may measure a subject with the already-known absorption coefficient $\mu_0$ and scattering coefficient $\mu_s'$ and predict the reflectance of an output light reflected from the subject. Then, the signal processing unit 130 substitutes the amplitudes of the measured output light and the predicted output light in Equation 3 to obtain $C_O$. However, in some embodiments, the body composition analyzing unit 140 may do not perform the operation of STEP 2-1. In this case, the signal processing unit 130 may receive the already determined $C_O$.

Referring to STEP 2 again, the body composition analyzing unit 140 compensates for error values caused by device itself (i.e., phase and amplitude caused by the device) from the measured output light R using the previously obtained $C_O$. Then, the body composition analyzing unit 140 can calculate a reflectance of the output light R obtained according to Equation 3.

STEP 3: The signal processing unit 130 can obtain a chromophore concentration of the subject to be measured by fitting the reflectance of the output light into the diffusion model of STEP 1. Herein, the body composition analyzing unit 140 may perform least square fitting to the amplitude and phase of the output light.

The body composition analyzing unit 140 can analyze constituent components in the subject 20 using the concentrations of the respective chromophores.

As described above, the bio-signal analyzing apparatus 10 according to an embodiment of the present disclosure provides a method of measuring a concentration of a chromophore using a predetermined number of light sources 110 and light measurement units 120.

FIG. 4 is a flowchart provided to explain a method of analyzing body composition according to an embodiment of the present disclosure.

Firstly, multiple light sources are driven based on a modulation signal whose frequency is modulated by the lock-in amplifier chip 131 (S410). As described above, the lock-in amplifier chip 131 generates predetermined modulation frequencies and sequentially supplies the modulation frequencies to the respective light sources.

Then, multiple light measurement units measure respective optical signals output from the multiple light sources and reflected from a subject (S420).

Then, the multiplexer 133 multiplexes light sensing signals measured by the respective multiple light measurement units and sequentially outputs the multiple light sensing signals (S430). In this case, the sequence to output the light sensing signals may be previously determined to identify which light measurement unit each light sensing signal is output from.

Then, the lock-in amplifier chip 131 receives the sequentially output multiple light sensing signals, performs demodulation thereto and then outputs them (S440).

Then, a process of analyzing body composition of the subject is performed based on the signals output from the lock-in amplifier chip 131 (S450). In this process, a reflectance at each discrete wavelength is calculated based on the signals output from the lock-in amplifier chip 131 and a concentration of a chromophore present in the subject is calculated based on the calculated reflectance. Details thereof have been described above.

The above-described signal processing method or body composition analyzing method according to an embodiment of the present disclosure can be embodied in a storage medium including instruction codes executable by a computer such as a program module executed by the computer. The storage medium includes a computer-readable medium, and the computer-readable medium can be any usable medium which can be accessed by the computer and includes all volatile/non-volatile and removable/non-removable media. Further, the computer-readable medium may include a computer storage medium. The computer storage medium includes all volatile/non-volatile and removable/non-removable media embodied by a certain method or technology for storing information such as computer-readable instruction code, a data structure, a program module or other data.

The above description of the present disclosure is provided for the purpose of illustration, and it would be understood by a person with ordinary skill in the art that various changes and modifications may be made without changing technical conception and essential features of the present disclosure. Thus, it is clear that the above-described embodiments are illustrative in all aspects and do not limit the present disclosure. For example, each component described to be of a single type can be implemented in a distributed manner. Likewise, components described to be distributed can be implemented in a combined manner.

The scope of the present disclosure is defined by the following claims rather than by the detailed description of the embodiment. It shall be understood that all modifications and embodiments conceived from the meaning and scope of the claims and their equivalents are included in the scope of the present disclosure.

We claim:

1. A signal processing device that processes a bio-signal, comprising:
   a lock-in amplifier chip configured to output one or more frequency-modulated modulation signals and enable one or more light sources to be driven in response to the modulation signals; and
   a multiplexer configured to receive and multiplex light sensing signals output from the light sources and then measured by multiple light measurement units,
   wherein the light sensing signals are output from the light sources driven by the one or more frequency-modulated modulation signals, and
   wherein the lock-in amplifier chip sequentially demodulates the multiple light sensing signals transmitted through the multiplexer.

2. The signal processing device of claim 1, further comprising:
   a differential amplifier provided between an output end of the multiplexer and an input end of the lock-in amplifier chip and configured to receive the output of the multiplexer and transmit the output to the lock-in amplifier chip.

3. The signal processing device of claim 1, further comprising:
   an analog-digital converter configured to convert the output of the lock-in amplifier chip into a digital signal.

4. The signal processing device of claim 1, further comprising:
   a light source driver configured to be driven based on the modulation signal, wherein the light source driver is configured to transmits a driving signal modulated based on the modulation signal to one or more light sources, and the light sensing signals contain a frequency component of the modulation signal.

5. The signal processing device of claim 4, further comprising:

multiple light measurement units configured to output the light sensing signals, respectively, wherein the light measurement units are configured to detect an output light of a light source driven by the light source driver.

6. The signal processing device of claim 5, further comprising:

multiple transimpedance amplifiers configured to convert the light sensing signals of the light measurement units into voltage signals and transmit the voltage signals to the multiplexer.

7. The signal processing device of claim 1, wherein the lock-in amplifier chip classifies and sequentially outputs modulation signals to the respective light sources according to a predetermined sequence, and the multiplexer transmits the light sensing signals measured by the respective light measurement units to the lock-in amplifier chip according to a predetermined sequence.

8. A body composition analyzing apparatus that analyzes a bio-signal, comprising:

multiple light sources;

multiple light measurement units;

a signal processing unit configured to transmit one or more frequency-modulated modulation signals to the light sources through a lock-in amplifier chip, receive light sensing signals measured by the light measurement units, and remove a noise from the light sensing signals through the lock-in amplifier chip; and a body composition analyzing unit configured to analyze body composition of a subject based on a signal output from the signal processing unit, wherein the signal processing unit includes:

the lock-in amplifier chip configured to output the frequency-modulated modulation signals;

a multiplexer configured to receive and multiplex the light sensing signals measured by the light measurement units; and the lock-in amplifier chip sequentially demodulates the multiple light sensing signals transmitted through the multiplexer;

wherein the light sensing signals are output from the light sources driven by the one or more frequency-modulated modulation signals.

9. The body composition analyzing apparatus of claim 8, further comprising:

a differential amplifier provided between an output end of the multiplexer and an input end of the lock-in amplifier chip and configured to receive the output of the multiplexer and transmit the output to the lock-in amplifier chip.

10. The body composition analyzing apparatus of claim 8, further comprising:

an analog-digital converter configured to convert the output of the lock-in amplifier chip into a digital signal and transmit the digital signal to the body composition analyzing unit.

11. The body composition analyzing apparatus of claim 8, further comprising:

a light source driver configured to be driven based on the modulation signal, wherein the light sensing signals contain a frequency component of the modulation signal.

12. The body composition analyzing apparatus of claim 8, further comprising:

multiple transimpedance amplifiers configured to convert the light sensing signals of the light measurement units into voltage signals and transmit the voltage signals to the multiplexer.

13. The body composition analyzing apparatus of claim 8, wherein the body composition analyzing unit is configured to calculate a reflectance at each discrete wavelength based on the signal transmitted from the signal processing unit and calculate a concentration of a chromophore present in the subject based on the reflectance at each discrete wavelength.

14. The body composition analyzing apparatus of claim 8, wherein the body composition analyzing unit is configured to determine the number and kinds of light sources and light measurement units to be driven from among the multiple light sources and the multiple light measurement units based on at least one of the number, content, and kind of a chromophore present in the subject.

15. The body composition analyzing apparatus of claim 8, wherein the lock-in amplifier chip classifies and sequentially outputs modulation signals to the respective light sources according to a predetermined sequence, and the multiplexer transmits the light sensing signals measured by the respective light measurement units to the lock-in amplifier chip according to a predetermined sequence.

16. The body composition analyzing apparatus of claim 8, wherein each of the light sources and each of the light measurement units form a pair facing each other.

17. A method of analyzing body composition by analyzing a bio-signal, comprising:

outputting optical signals by multiple light sources based on one or more frequency-modulated modulation signals whose frequency is modulated by a lock-in amplifier chip;

measuring the optical signals, which are output from the multiple light sources and reflected from a subject, by multiple light measurement units, respectively;

multiplexing multiple light sensing signals measured by the respective multiple light measurement units and then sequentially outputting the multiple light sensing signals by a multiplexer;

receiving, demodulating, and outputting the sequentially output multiple light sensing signals by the lock-in amplifier chip; and analyzing body composition of a subject based on the signals output from the lock-in amplifier chip, wherein the light sensing signals are output from the light sources driven by the one or more frequency-modulated modulation signals.

18. The method of analyzing body composition of claim 17, further comprising:

identifying each light sensing signal in synchronization with timing to output each light sensing signal from the multiplexer.

19. The method of analyzing body composition of claim 17, wherein the analyzing of the body composition includes calculating a reflectance at each discrete wavelength based on the signals output from the lock-in amplifier chip and calculating a concentration of a chromophore present in the subject based on the reflectance at each discrete wavelength.

\* \* \* \* \*